(12) United States Patent
Brandlhuber (10) Patent No.: US 10,281,440 B2
(45) Date of Patent: May 7, 2019

(54) CLAMPING DEVICE FOR A SAMPLE PREPARATION

(71) Applicant: LCTech GmbH, Obertaufkirchen (DE)

(72) Inventor: Martin Brandlhuber, St. Wolfgang (DE)

(73) Assignee: LCTECH GMBH, Obertaufkirchen (DE)

( * ) Notice: Subject to any disclaimer, the term of this patent is extended or adjusted under 35 U.S.C. 154(b) by 0 days.

(21) Appl. No.: 15/459,277

(22) Filed: Mar. 15, 2017

(65) Prior Publication Data

US 2017/0322189 A1 Nov. 9, 2017

(30) Foreign Application Priority Data

May 4, 2016 (DE) .................. 10 2016 108 357

(51) Int. Cl.
| | | |
|---|---|---|
| G01N 30/60 | (2006.01) |
| B01D 15/22 | (2006.01) |
| B25B 5/00 | (2006.01) |
| B25B 1/18 | (2006.01) |
| F16B 2/12 | (2006.01) |
| F16B 2/18 | (2006.01) |
| B25B 1/02 | (2006.01) |
| B25B 1/24 | (2006.01) |
| B25B 5/06 | (2006.01) |
| B25B 5/16 | (2006.01) |
| G01N 30/88 | (2006.01) |

(52) U.S. Cl.
CPC ......... *G01N 30/6047* (2013.01); *B01D 15/22* (2013.01); *B25B 1/02* (2013.01); *B25B 1/18* (2013.01); *B25B 1/2478* (2013.01); *B25B 5/00* (2013.01); *B25B 5/003* (2013.01); *B25B 5/061* (2013.01); *B25B 5/068* (2013.01); *B25B 5/166* (2013.01); *F16B 2/12* (2013.01); *F16B 2/185* (2013.01); *G01N 30/6039* (2013.01); *G01N 30/6034* (2013.01); *G01N 2030/8881* (2013.01)

(58) Field of Classification Search
None
See application file for complete search history.

(56) References Cited

U.S. PATENT DOCUMENTS

| | | | | |
|---|---|---|---|---|
| 3,615,235 A | * | 10/1971 | Hrdina ....................... B01J 8/06 |
| | | | | 165/179 |
| 4,732,672 A | * | 3/1988 | Kiang .................... G01N 30/22 |
| | | | | 210/198.2 |
| 8,307,541 B2 | | 11/2012 | Ford | |

(Continued)

*Primary Examiner* — Jill A Warden
*Assistant Examiner* — Brittany I Fisher
(74) *Attorney, Agent, or Firm* — Renner Kenner Greive Bobak Taylor & Weber (57) ABSTRACT

The clamping device according to the invention for clamping at least two processing devices for a sample preparation is made up essentially of at least three clamping blocks arranged in the axial direction, at least two of which are designed as movable clamping blocks, and a displacement mechanism for displacing the movable clamping blocks between an open position for inserting the processing devices, and a clamping position in which the at least two processing devices are clamped one on top of the other in the axial direction between two clamping blocks in each case. The displacement mechanism is designed for displacing the at least two movable clamping blocks in opposite directions.

11 Claims, 6 Drawing Sheets

(56) References Cited

U.S. PATENT DOCUMENTS

| | | |
|---|---|---|
| 9,433,876 B2 | 9/2016 | Baumann |
| 2010/0154207 A1* | 6/2010 | Ford ................. G01N 30/6004 29/700 |
| 2013/0206653 A1 | 8/2013 | Brann |
| 2014/0231330 A1* | 8/2014 | Baumann ............. G01N 30/461 210/198.2 |

* cited by examiner

CLAMPING DEVICE FOR A SAMPLE PREPARATION

TECHNICAL FIELD

The invention relates to a clamping device for clamping at least two processing devices for a sample preparation, in particular for analyzing chemical substances, for example for chromatography.

BACKGROUND OF THE INVENTION

A space-saving, flexible, and easy to use clamping device for clamping multiple columns for a sample preparation is known from EP 2 767 828 B1, for example. The clamping device has multiple clamping blocks and a displacement mechanism for displacing a clamping block relative to an oppositely situated clamping block between an open position and a clamping position. In the open position, a column may be attached between two oppositely situated clamping blocks, while in the clamping position the inserted column is clamped between the oppositely situated clamping blocks in order to establish a fluid connection between the column and at least one of the oppositely situated clamping blocks. At least three clamping blocks are supported one behind the other in a row on a guide track, so that at least two columns may be clamped, one behind the other in the axial direction, between the clamping blocks. The slidable clamping blocks supported on the guide track are connected to the displacement mechanism via coupling means in such a way that actuation of the displacement mechanism from the clamping position into the open position causes displacement of all slidable clamping blocks, and in the process the columns are released.

Due to the arrangement of the clamping blocks on the guide track, the clamping device may be adapted very quickly and easily to different column lengths. Another advantage of the axial arrangement is that the fluid connection between the columns is comparatively short, if this is desired.

In the described embodiment, one of the clamping blocks is stationarily situated on the guide track, while at least two additional clamping blocks are slidably supported on the guide track. The clamping block stationarily situated on the guide track forms one end of the row of clamping blocks situated one behind the other, while at least the last slidable clamping block at the other end of the row is in operative connection with the displacement mechanism in order to displace it relative to the stationary clamping block. A displacement of the slidable clamping block, connected to the displacement mechanism, in the direction of the stationary clamping block also brings about a displacement of all clamping blocks situated in between, together with the inserted columns, until the clamping position is reached. It is thus possible to clamp a plurality of columns in a liquid-tight manner by displacing one clamping block. To limit the pressure generated by the clamping blocks on the columns, the displacement mechanism may have at least one force-limiting compensating spring, a displacement force generated by the displacement mechanism being transmitted to the at least one slidable clamping block via the compensating spring. Due to this compensating spring, the clamping force transmitted to the columns is limited, and overload/damage to the columns is thus avoided.

SUMMARY OF THE INVENTION

The object of the invention is to improve the handling of the clamping device, in particular for automated placement.

According to the invention, this object is achieved by the features of claim 1, in that the displacement mechanism is designed for displacing the at least two movable clamping blocks in opposite directions.

The clamping device according to the invention for clamping at least two processing devices for a sample preparation is made up essentially of at least three clamping blocks arranged in the axial direction, at least two of which are designed as movable clamping blocks, and a displacement mechanism for displacing the movable clamping blocks between an open position for inserting the processing devices, and a clamping position in which the at least two processing devices are clamped one on top of the other in the axial direction between two clamping blocks in each case. The displacement mechanism is designed for displacing the at least two movable clamping blocks in opposite directions.

Filters, columns, or cartridges, for example, are used as processing devices.

According to one preferred embodiment of the invention, at least two pairs of clamping blocks are each provided with two of the clamping blocks which are movable in opposite directions, each clamping block pair being designed for accommodating a respective processing device between the two oppositely movable clamping blocks. This embodiment is particularly suited for automated placement or removal of the processing devices, since the processing device may be introduced into or removed from the clamping device with a linear movement. However, if one of the two clamping blocks of a pair of clamping blocks is provided as a stationary clamping block, automated placement is still possible, but for this purpose the processing device must be moved in two directions.

Furthermore, the movable clamping blocks are preferably slidably supported on a guide profile. The displacement mechanism may also have a first coupling means and a second coupling means, in each case a movable clamping block of each clamping block pair being in operative contact with the first coupling means, and the respective other movable clamping block of each clamping block pair being in operative contact with the second coupling means. In particular, the first and the second coupling means may be oppositely displaceable in the axial direction.

For achieving the opposite displaceability of the at least two movable clamping blocks, according to the preferred exemplary embodiment the first and the second coupling means are connected to one another via a two-sided lever arm that is suspended on a pivot point. The displacement mechanism may also have an actuator for displacing the first and the second coupling means in opposite directions, the actuator being in operative connection with the two-sided lever arm in order to rotate it about its pivot point.

According to another embodiment of the invention, at least one, preferably both of, the movable clamping blocks of each clamping block pair is/are connected to the associated coupling means via at least one elastic compensation element. The clamping force acting on the processing device which is clamped between the clamping blocks of a pair of clamping blocks may be limited in this way. The clamping force may also be individually adapted to the particular processing device by the elastic compensation element. It is thus conceivable in particular to use compensation elements having different elastic forces for pairs of clamping blocks situated one on top of the other.

According to another embodiment of the invention, the first and the second coupling means may have a rod-like design, the movable clamping blocks having through holes through which the rod-like coupling means are passed. The movable clamping blocks are then connected to one of the two coupling means in each case via a carrier element, for example. However, two carrier elements are preferably provided, so that they carry along the movable clamping blocks in both movement directions.

Depending on the type of processing device to be used, at least one of the movable clamping blocks of each clamping block pair has a closure element for closing the processing device in a gas- and liquid-tight manner.

BRIEF DESCRIPTION OF THE DRAWINGS

Further advantages and embodiments of the invention are described in greater detail below with reference to several exemplary embodiments and the drawings, which show the following.

DETAILED DESCRIPTION OF ILLUSTRATIVE EMBODIMENTS

Figures 1A, 1B:
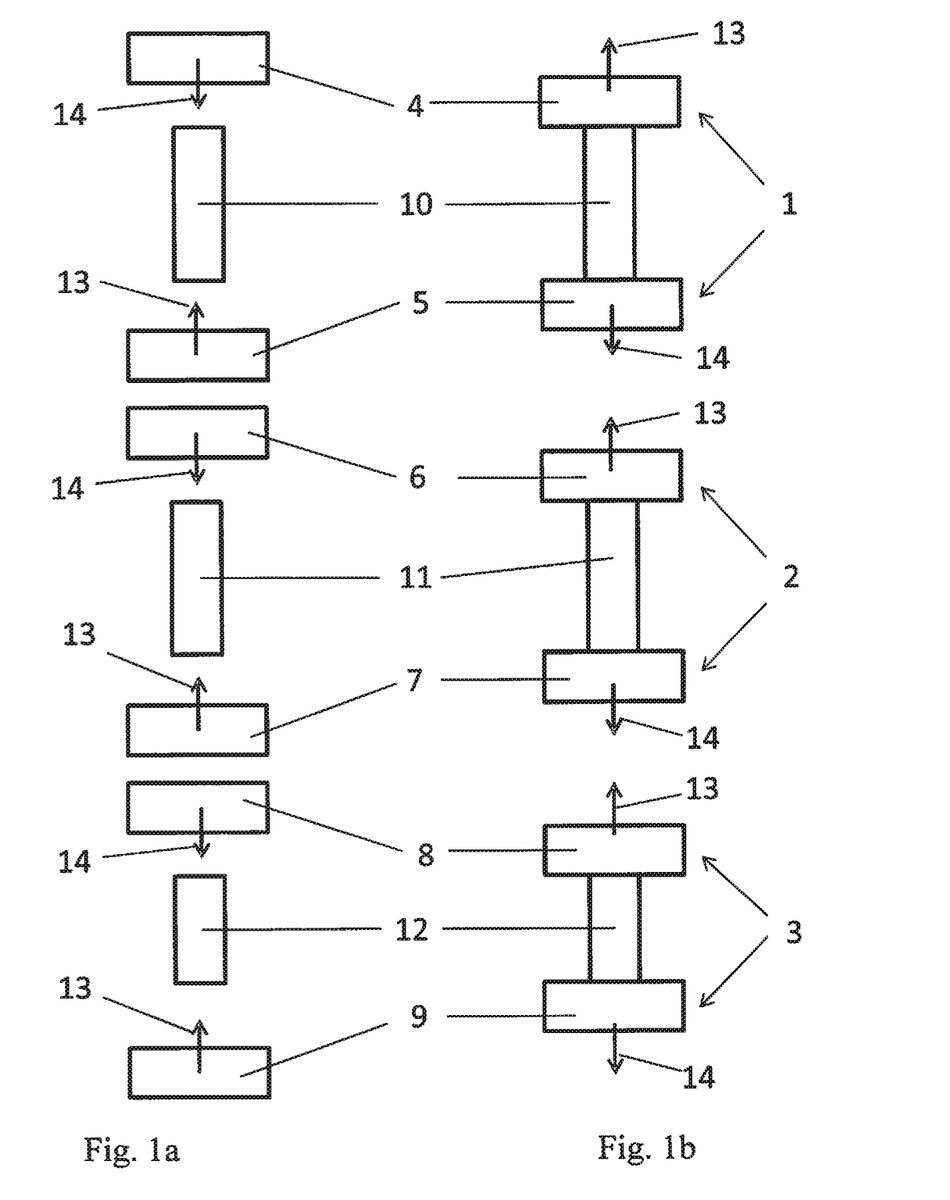
FIG. 1a shows a schematic illustration of the clamping device according to a first exemplary embodiment, in the open position.
FIG. 1b shows a schematic illustration of the clamping device according to FIG. 1a, in the clamping position.

FIG. 1a shows a clamping device according to a first exemplary embodiment. The clamping device has three pairs of clamping blocks 1, 2, 3, each having two movable clamping blocks 4, 5; 6, 7; 8, 9, respectively, situated one on top of the other in the axial direction.

A displacement mechanism, not illustrated in greater detail here, is used for displacing the movable clamping blocks 4 through 9 between the open position, shown in FIG. 1a, for inserting a processing device 10, 11, 12, respectively, and a clamping position, shown in FIG. 1b, in which the processing devices 10, 11, 12 are clamped one on top of the other in the axial direction between two clamping blocks in each case. For this purpose, the clamping blocks of each pair of clamping blocks are displaced in opposite directions (arrows 13, 14). When the displacement mechanism is actuated from the clamping position, shown in FIG. 1b, into the open position shown in FIG. 1a, the clamping blocks of each pair of clamping blocks are in turn displaced in opposite directions, so that the distance between the associated clamping blocks is increased and the processing device is released.

The displacement mechanism 15 is explained in greater detail below with reference to FIGS. 2a, 2b, 3a, and 3b. The clamping blocks 4 through 9 are slidably supported on a guide profile 16. The displacement mechanism has a first coupling means 17 and a second coupling means 18 which have a rod-shaped design, in each case a movable clamping block of each pair of clamping blocks being in operative contact with the first coupling means 17, and the respective other movable clamping block of each pair of clamping blocks being in operative contact with the second coupling means. In the illustrated exemplary embodiment, the clamping blocks 4, 6, and 8 are connected to the first coupling means 17 via two carrier elements 19, 20 in each case, while the clamping blocks 5, 7, and 9 are connected to the second coupling means 18 via two carrier elements 21, 22 in each case. Each clamping block is provided with two through holes 23, 24 through which the rod-like coupling means 17, 18 are passed. The second coupling means 18 is merely passed through the clamping blocks 4, 6, and 8, and exerts no carrier effect on these clamping blocks. In the area of the clamping blocks 5, 7, and 9, the second coupling means 18 has carrier elements 21, 22 in each case which carry along the clamping blocks when the second coupling means 18 is moved in the direction of its extension. Correspondingly, the first coupling means 17 is merely passed through the clamping blocks 5, 7, and 9 without a carrier effect, whereas it is in operative contact with the clamping blocks 4, 6, and 8 via the carrier elements 19, 20.

Figure 2A:
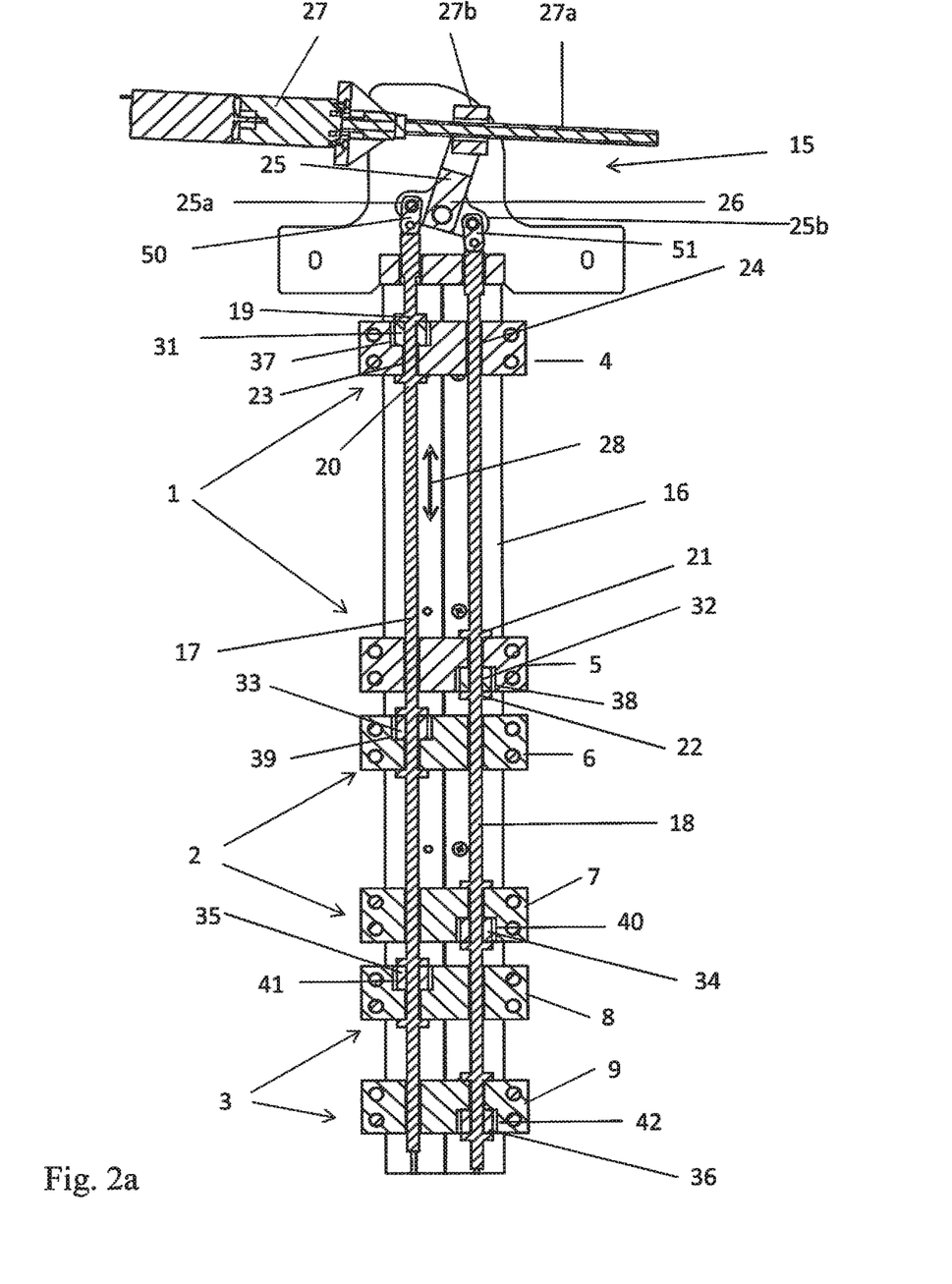
FIG. 2a shows a sectional rear view of the clamping device according to FIG. 1a, FIG. 2b shows a sectional rear view of the clamping device according to FIG. 1b.
Figure 2B:
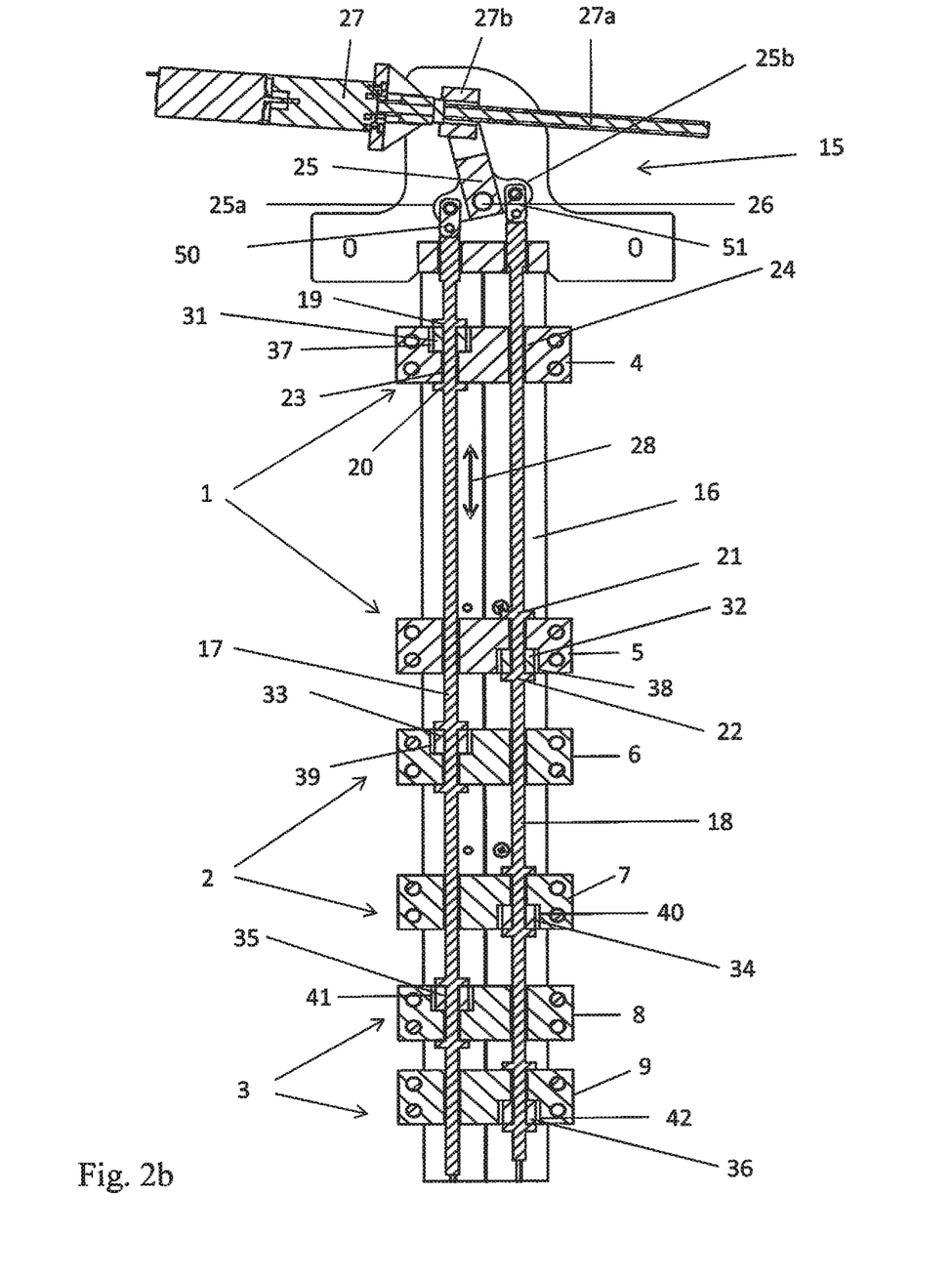

To achieve the opposite movement of the clamping blocks of each pair of clamping blocks, the two coupling means 17, 18 must be appropriately actuated in opposite directions. This takes place in that a two-sided lever arm 25 is provided, which is rotatable about its pivot point 26 by means of an actuator 27. The first coupling means 17 is articulatedly connected to a first lever arm 25a of the two-sided lever arm 25, and the second coupling means 18 is articulatedly connected to a second lever arm 25b of the two-sided lever arm 25. The coupling means 17, 18 are articulatedly connected to the first lever arm 25a and to the second lever arm 25b via compensation pieces 50, 51, respectively.

The actuator 27 is designed as a linear actuator, for example, having a nut 27b that is displaceable on a spindle 27a. The nut 27b in turn is connected to the two-sided lever arm in such a way that a displacement of the nut 27b on the spindle 27a causes rotation of the two-sided lever arm 25 about its pivot point 26, as is apparent from a comparison of FIGS. 2a and 2b. Rotation of the lever arm 25 about its pivot point 26 brings about an opposite displacement of the first and second coupling means 17, 18 in the axial direction along the double arrow 28. When the displacement mechanism 15 is actuated from the open position, shown in FIG. 2a, into the clamping position shown in FIG. 2b, the first coupling means together with the clamping blocks 4, 6, and 8 is moved downwardly, and the second coupling means together with the clamping blocks 5, 7, and 9 is moved upwardly, so that the distance between the clamping blocks 4, 5; 6, 7; 8, 9 associated with a clamping block pair is correspondingly decreased.

Figure 3A:
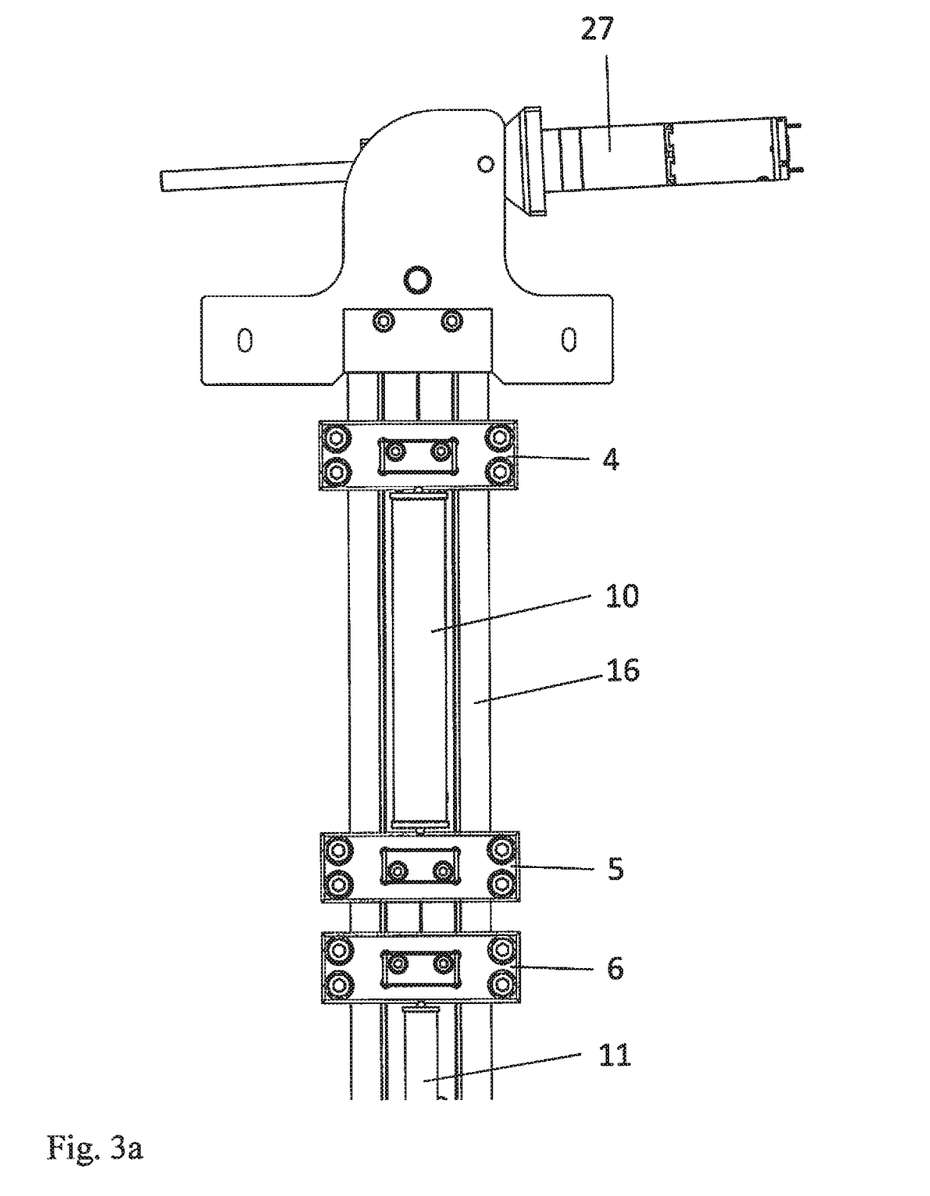
FIG. 3a shows a sectional front view of the clamping device according to FIG. 2a, FIG. 3b shows a sectional front view of the clamping device according to FIG. 2b.
Figure 3B:
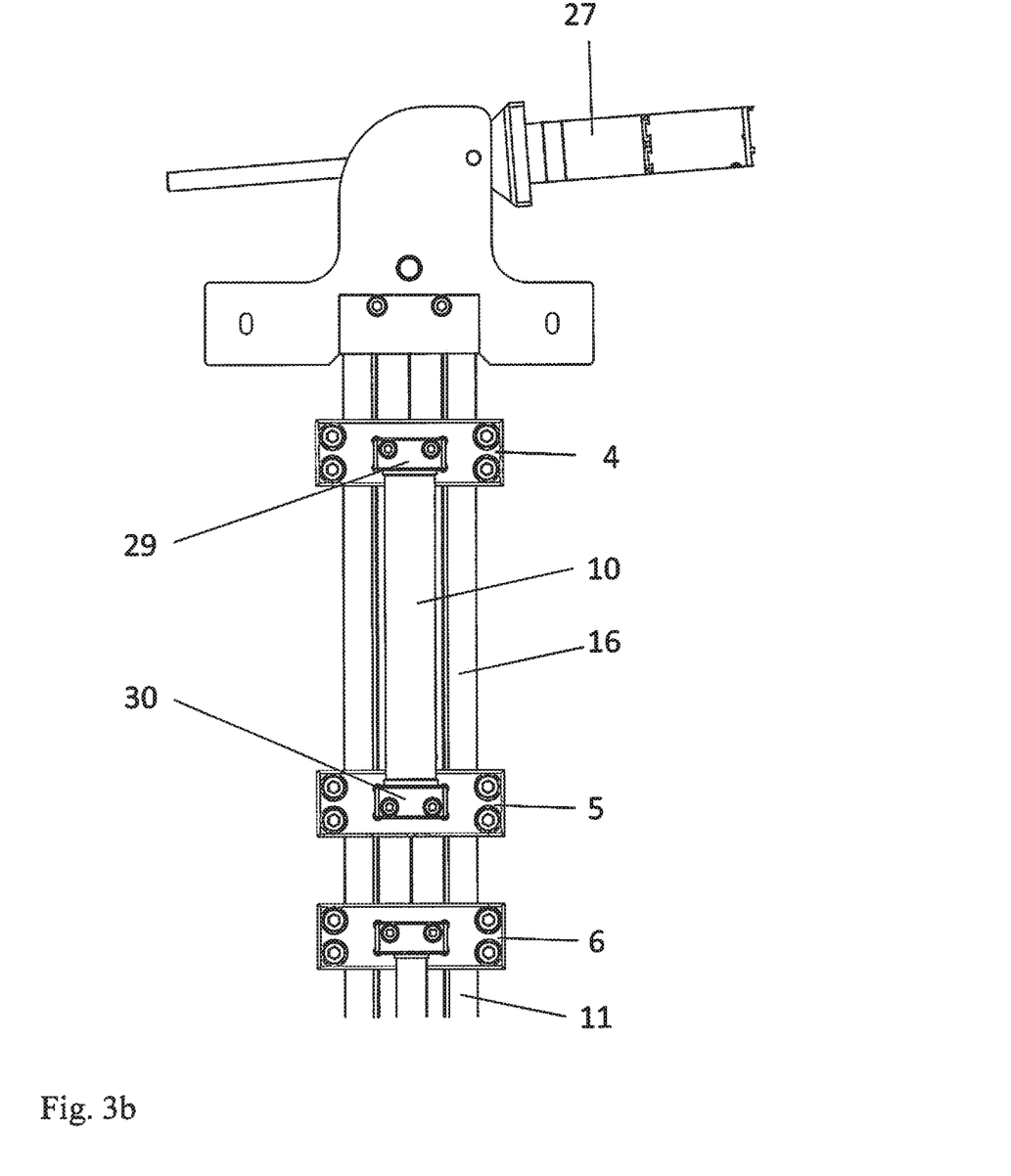

FIGS. 3a and 3b show the situation on the opposite side of the clamping device, to which the processing devices 10, 11, 12 may be attached or from which they may be removed. In each case a clamping block of each pair of clamping blocks has a first support and closure element 29, and the respective other clamping block has a second support and closure element 30, which in each case are designed for supporting and/or closing the processing device 10. The processing device usually has an open design at its top side, so that the first support and closure element 29 is designed for closing the processing device in a gas- and liquid-tight manner. The supporting and/or closing element 29 may be designed in particular as a nonself-locking cone which brings about a gas- and liquid-tight closure of the processing device when the associated clamping blocks are brought together. The second support and closure element 30 is usually used only for supporting the processing device 10, and may likewise have a conical design.

In order for the processing devices in the clamping position on the one hand to be acted on with sufficient pressure to ensure the gas- and liquid-tight seal, and on the other hand to avoid damaging the processing device at an excessively high pressure, the clamping blocks are in operative connection with the first and second coupling means 17, 18 via elastic compensation elements 31 through 36. The elastic compensation elements may be designed, for example, as coil springs or elastomeric elements. In principle, it would be sufficient for one clamping block of a pair of clamping blocks in each case to be designed with such a compensation element. The elastic force of the elastic compensation elements is adapted to the processing device to be clamped. If different processing devices are supported in the superposed pairs of clamping blocks, elastic compensation elements having different strengths may also accordingly be used. It may thus be ensured that the processing devices are acted on only by the pressure that is sufficient for the gas- and liquid-tight seal, but which does not result in damage to same. In the illustrated exemplary embodiment, the elastic compensation elements are situated in recesses 37 through 42 in the clamping blocks, with the axes of the through holes 23, 24, of the recesses 37 through 42, and of the two coupling means being in alignment.

Figures 4A, 4B:
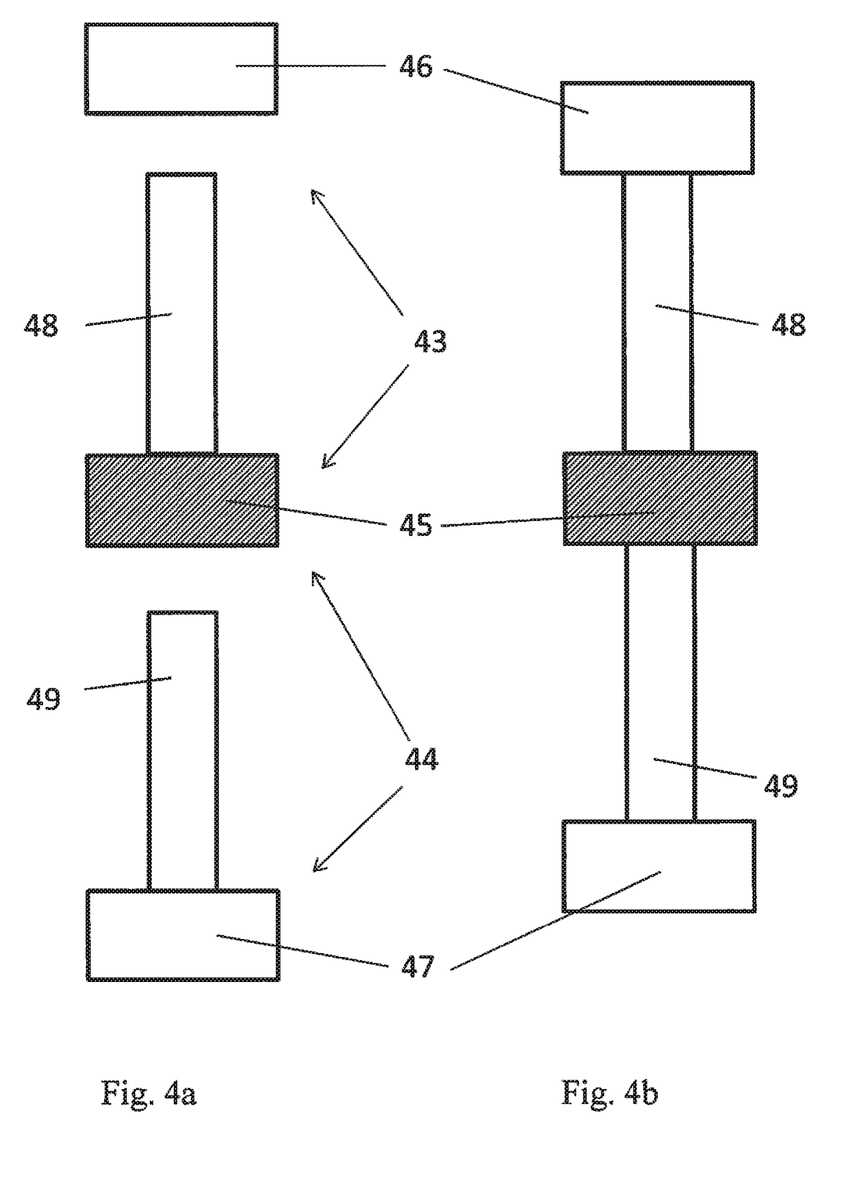
FIG. 4a shows a schematic illustration of the clamping device according to a second exemplary embodiment, in the open position.
FIG. 4b shows a schematic illustration of the clamping device according to a second exemplary embodiment, in the clamping position.

FIGS. 4[a] and 4b show another schematic illustration of a second exemplary embodiment, in which two or more pairs of clamping blocks 43, 44 are provided, each of which is made up a stationary clamping block 45 and a movable clamping block 46 and 47, respectively. In the illustrated exemplary embodiment, the stationary clamping block 45 is utilized for both pairs of clamping blocks. However, it is also conceivable for each clamping block pair to have its own stationary clamping block. Each clamping block pair 43, 44 is used for clamping a processing device 48, 49, respectively. The same as with the preceding exemplary embodiment, the two movable clamping blocks 46, 47 are displaceable in opposite directions from the open position (FIG. 4a) into the clamping position (FIG. 4b), and vice versa.

In addition, the above-described displacement mechanism and the at least one elastic compensation element associated with each clamping block pair may also be used here corresponding to the exemplary embodiment described above.

The invention claimed is:

1. A clamping device for clamping at least two processing devices for a sample preparation, comprising
   at least four clamping blocks arranged in the axial direction and forming a first clamping block pair and a second clamping block pair, each of said first and second clamping block pairs being formed of oppositely movable clamping blocks defined by two of said at least four clamping blocks that are movable in opposite directions, each clamping block pair accommodating a respective processing device between the oppositely movable clamping blocks;
   a displacement mechanism for displacing in opposite directions the oppositely movable clamping blocks of the first clamping block pair and the second clamping block pair between an open position for inserting the processing devices, and a clamping position in which the at least two processing devices are clamped one on top of the other in the axial direction,
   a first one of said at least two processing devices being held between the movable clamping blocks of said first clamping block pair and a second one of said at least two processing devices being held between the movable clamping blocks of said second clamping block pair, wherein the displacement mechanism includes:
      a first coupling means,
      a second coupling means, wherein a first movable clamping block of each of the first and second clamping block pairs is in operative contact with the first coupling means, and a second movable clamping block of each of the first and second clamping block pairs is in operative contact with the second coupling means.

2. The clamping device according to claim 1, characterized in that the movable clamping blocks are slidably supported on a guide profile.

3. The clamping device according to claim 1, characterized in that the first and the second coupling means are displaceable in opposite directions in the axial direction.

4. The clamping device according to claim 3, characterized in that the first and the second coupling means have a rod-like design, and the movable clamping blocks have through holes through which the rod-like coupling means are passed.

5. The clamping device according to claim 3, characterized in that the first and the second coupling means are connected to one another via a two-sided lever arm that is suspended on a pivot point.

6. The clamping device according to claim 5, characterized in that the actuator is in operative connection with the two-sided lever arm in order to rotate it about the pivot point.

7. The clamping device according to claim 1, characterized in that the displacement mechanism has an actuator for displacing the first and the second coupling means in opposite directions.

8. The clamping device according to claim 1, characterized in that at least one of the movable clamping blocks of each of the first and second clamping block pairs is operatively connected to the associated first or second coupling means via at least one elastic compensation element.

9. The clamping device according to claim 1, characterized in that the movable clamping blocks of each of the first and second clamping block pairs are operatively connected to one of the first and second coupling means in each case via at least one carrier element.

10. The clamping device according to claim 1, characterized in that at least one of the movable clamping blocks of each of the first and second clamping block pairs has a closure element for closing the processing device in a gas- and liquid-tight manner.

11. The clamping device according to claim 1, characterized in that both clamping blocks of the movable clamping blocks of each of the first and second clamping block pairs are operatively connected to the associated first or second coupling means via at least one elastic compensation element.

* * * * *